(12) United States Patent
Sadler et al.

(10) Patent No.: US 8,999,143 B2
(45) Date of Patent: Apr. 7, 2015

(54) HIGH TEMPERATURE CCR PROCESS WITH INTEGRATED REACTOR BYPASSES

(71) Applicant: UOP LLC, Des Plaines, IL (US)

(72) Inventors: Clayton C. Sadler, Arlington Heights, IL (US); Mark D. Moser, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/539,582

(22) Filed: Nov. 12, 2014

(65) Prior Publication Data

US 2015/0073189 A1    Mar. 12, 2015

Related U.S. Application Data

(62) Division of application No. 13/682,061, filed on Nov. 20, 2012, now Pat. No. 8,900,442.

(51) Int. Cl.
| | |
|---|---|
| C10G 35/04 | (2006.01) |
| C10G 35/24 | (2006.01) |
| C07C 5/367 | (2006.01) |
| C07C 5/41 | (2006.01) |

(52) U.S. Cl.
CPC .............. *C07C 5/417* (2013.01); *C07C 5/367* (2013.01); *C07C 2521/04* (2013.01); *C07C 2521/08* (2013.01); *C07C 2521/12* (2013.01); *C07C 2523/02* (2013.01); *C07C 2523/06* (2013.01); *C07C 2523/08* (2013.01); *C07C 2523/12* (2013.01); *C07C 2523/14* (2013.01); *C07C 2523/26* (2013.01); *C07C 2523/42* (2013.01); *C07C 2523/44* (2013.01); *C07C 2523/46* (2013.01); *C07C 2529/068* (2013.01)

(58) Field of Classification Search
USPC ..................... 208/63, 64, 65, 133, 134, 141
See application file for complete search history.

(56) References Cited

U.S. PATENT DOCUMENTS 7,638,664 B2 * 12/2009 Peters et al. ................. 585/310

* cited by examiner

*Primary Examiner* — Thuan D Dang

(57) ABSTRACT

A process is presented for increasing the aromatics content in a reformate process stream. The process modifies existing processes to change the operation without changing the reactors or heating units. The process includes bypasses to utilize heating capacity of upstream heating units, and passes the excess capacity of the upstream heating units to downstream process streams.

5 Claims, 2 Drawing Sheets

US 8,999,143 B2

HIGH TEMPERATURE CCR PROCESS WITH INTEGRATED REACTOR BYPASSES

CROSS REFERENCE TO RELATED APPLICATION

This application is a Division of copending U.S. application Ser. No. 13/682,061 which was filed on Nov. 20, 2012, the contents of which are hereby incorporated by reference in its entirety.

FIELD OF THE INVENTION

The present invention relates to processes for the production of aromatic compounds from a hydrocarbon stream. In particular, the process is an improvement to increase the amount of aromatic compounds such as benzene, toluene and xylenes in a hydrocarbon feedstream.

BACKGROUND OF THE INVENTION

The reforming of petroleum raw materials is an important process for producing useful products. One important process is the separation and upgrading of hydrocarbons for a motor fuel, such as producing a naphtha feedstream and upgrading the octane value of the naphtha in the production of gasoline. However, hydrocarbon feedstreams from a raw petroleum source include the production of useful chemical precursors for use in the production of plastics, detergents and other products.

The upgrading of gasoline is an important process, and improvements for the conversion of naphtha feedstreams to increase the octane number have been presented in U.S. Pat. Nos. 3,729,409; 3,753,891; 3,767,568; 4,839,024; 4,882,040; and 5,242,576. These processes involve a variety of means to enhance octane number, and particularly for enhancing the aromatic content of gasoline.

While there is a move to reduce the aromatics in gasoline, aromatics have many important commercial uses. Among them include the production of detergents in the form of alkyl-aryl sulfonates, and plastics. These commercial uses require more and purer grades of aromatics. The production and separation of aromatics from hydrocarbons streams are increasingly important.

Processes include splitting feeds and operating several reformers using different catalysts, such as a monometallic catalyst or a non-acidic catalyst for lower boiling point hydrocarbons and bi-metallic catalysts for higher boiling point hydrocarbons. Other improvements include new catalysts, as presented in U.S. Pat. Nos. 4,677,094; 6,809,061; and 7,799,729. However, there are limits to the methods and catalysts presented in these patents, and which can entail significant increases in costs.

Improved processes are needed to reduce the costs and energy usage in the production of aromatic compounds.

SUMMARY OF THE INVENTION

The present invention is a process for the reformation of hydrocarbons in a hydrocarbon process stream. In particular, the present invention is for the improvement of existing systems to increase the aromatic content of a hydrocarbon feedstream. The process includes the change in operation of an existing system of reforming reactors, and the redirection of process streams within a reforming reactor system.

The process is for increasing the aromatics content of the hydrocarbon stream, and includes passing the hydrocarbon stream through a series of reactors and reactor feed heaters. The process includes operating the first reactor at a lower temperature, and passing the excess capacity of the heating units for the first feedstream to downstream flows. The heated feedstream is split into at least two portions, and the first portion is passed to a reforming reactor. The second portion is passed to a downstream reactor effluent stream and is further heated for passing a feedstream with added heat to a downstream reactor.

In one embodiment, the first reactor is operated at a first inlet temperature, and the subsequent downstream reactors are operated at a temperature that is greater than the first inlet temperature.

In one embodiment, the process stream is split before the first reactor heater, and a portion is heated to a temperature greater than the first reactor inlet temperature. The heated portion is further split to pass a portion downstream, while mixing another portion with the unheated portion to form the first reactor feedstream.

Other objects, advantages and applications of the present invention will become apparent to those skilled in the art from the following detailed description and drawings.

DETAILED DESCRIPTION OF THE INVENTION

Figure 1:
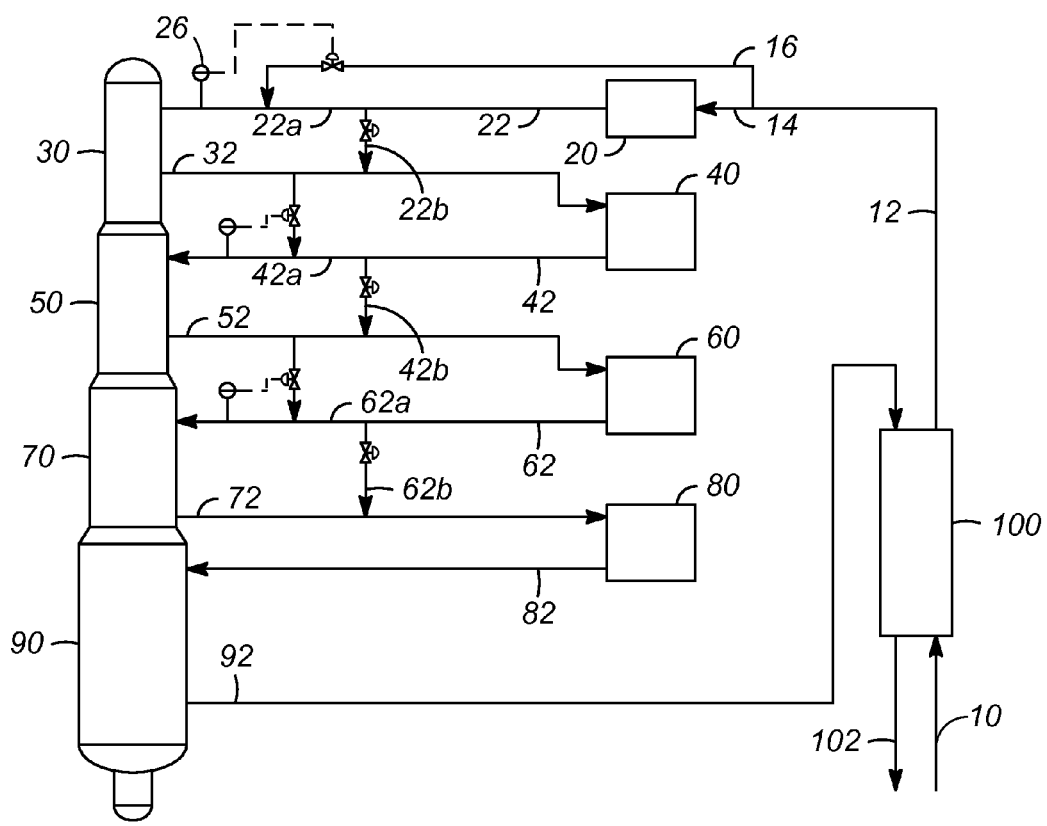
FIG. 1 is a diagram of a first embodiment of the invention for utilizing upstream reactors to heat feed for downstream processing.

The present invention is directed to improving the yields of aromatics from a hydrocarbon feedstream. In particular, the improvement is for a naphtha feedstream where the hydrocarbons are reformed to increase the yields of aromatics in the C6 to C8 range. The process is aimed at improving existing processes without the requirement of building new equipment. The present invention increases the production of aromatics in existing hydrocarbon reforming units. This is done by reducing the inlet temperature to a first reactor, and increasing the inlet temperature of the reactor feeds to downstream reactors. This shifts the heating duty of upstream heating units to downstream reactors, without the need to replace existing heating units or reactors.

There is an increased demand for aromatics. Important aromatics include benzene, toluene, and xylenes. These aromatics are important components in the production of detergents, plastics, and other high value products. With increasing energy costs, energy efficiency is an important aspect for improving the yields of aromatics. The present invention provides for understanding the differences in the properties of the different components in a hydrocarbon mixture to develop a better process.

The dehydrogenation and aromatization process of converting hydrocarbon streams lean in aromatics to hydrocarbon streams rich in aromatics is an endothermic process with the addition of energy to maintain useful reaction temperatures. The process requires a series of reactors with reactor interheaters. One of the problems is the ability to provide sufficient downstream heat to the process stream. The present invention allows for the shifting of heating loads on a process stream to downstream reactors without replacing expensive heaters or reactors.

A hydrocarbon stream is comprised of many constituents, and each constituent behaves differently under different conditions. The constituents can be divided into larger classes of compounds, where one class, such as paraffins, comprises many different paraffinic compounds. The dehydrogenation process is an endothermic process which requires a continuous input of energy to heat the process stream in the reactor. The greater the endothermicity, the greater the temperature drop within the reactor, and therefore the greater the amount of heat that is to be added to maintain the reaction. The dropping of temperature reduces the reaction rate and reduces the conversion. This requires additional heat to maintain a desired reaction rate.

Among the constituents in the hydrocarbon stream, the amount of endothermicity varies considerably. Energy usage in the dehydrogenation process can be reduced by separating out the individual constituents, but would be increased in the endeavor to separate the constituents. However, the reaction rates for the different constituents, and for the different classes of compounds varies. These variations change with temperature, such that different reactions, and different operating temperatures allow for a partial selectivity of the dehydrogenation process over some constituents and classes of compounds.

Compounding problems in the dehydrogenation process are the conversion rates for some of the constituents. In order to achieve good conversion of C6 and C7 paraffins to aromatic compounds, high temperatures and relatively short contact times are required. With the high endothermicity, control and maintenance of high reaction temperatures can be difficult. The hydrocarbon stream of primary interest is a full boiling range naphtha having olefins, naphthenes, paraffins, and aromatics, and the process is aimed at converting the non-aromatics to higher value aromatic compounds.

The present invention provides bypasses to shift the excess duty available in upstream heaters, such as a charge heater, or combined feed exchanger, to downstream reactor feeds. The reactor section bypasses reduces the required modifications to downstream reactors in order to operate at higher reactor inlet temperatures.

In one embodiment of the present invention, the process includes passing a hydrocarbon process stream through a series of reactors and reactor feed heaters. At least one of the heated feed streams is split into at least two portions. A first portion is passed to a corresponding reactor to generate a reactor effluent stream. The second portion is combined with a downstream reactor effluent stream, and the combined stream is passed to a downstream reactor feed heater to generate a downstream reactor feedstream. The last reactor in the series generates a product stream that has an increased aromatics content.

The new process shifts the temperatures of the feedstreams to the reactors with the first reactor operated at a first temperature, and subsequent reactors in the series operated at a temperature that is greater than the first temperature.

In one optional configuration, the process includes splitting at least one reactor effluent stream into at least two portions, a first portion and a second portion. The first portion of the effluent stream is passed with a second portion of an upstream heated feedstream to a reactor interheater. The second portion of the effluent stream is combined with a downstream heated feedstream and passed to a downstream reactor. The downstream reactor can be the next reactor in the series, or the downstream can be the second reactor downstream of the effluent stream.

In one embodiment, the process is as shown in FIG. 1. This embodiment utilizes four reactors for the reforming process, but can be expanded to include more reactors, or adjusted to operate with fewer reactors. The process includes passing a hydrocarbon process stream 10 through a charge heater 20 to generate a first heated feedstream 22. The heated feedstream 22 is split into two portions, a first portion 22a and a second portion 22b. The first portion 22a is passed to a first reactor 30 to generate a first effluent stream 32. The first effluent stream 32 is combined with the second portion 22b and passed through a first reactor interheater 40 to generate a second heated feedstream 42. The second heated feedstream 42 is split into two portions, a first portion 42a and a second portion 42b. The first portion 42a is passed to a second reactor 50 to generate a second effluent stream 52. The second effluent stream 52 is combined with the second portion 42b and passed to a second reactor interheater 60 to generate a third heated feedstream 62. The third heated feedstream 62 is split into two portions, a first portion 62a and a second portion 62b. The first portion is passed through a third reactor 70 to generate a third effluent stream 72. The third effluent stream 72 is combined with the second portion 62b and passed to a third reactor interheater 80 to generate a fourth heated feedstream 82. The fourth heated feedstream 82 is passed to a fourth reactor 90 to generate a product stream 92.

The process of the present invention can include additional bypasses to provide further control of the inlet temperatures, and to increase the ability to pass head duty to downstream reactor feeds. In a variation, the process includes passing the product stream 92 through a combined feed heat exchanger 100 to generate a cooled product stream 102. The feedstream 10 is preheated to generate a preheated feedstream 12. The preheated feedstream 12 can be split into two portions, a first portion 14 and a second portion 16. The first portion 14 is passed through the charge heater 20 to heat the feedstream 14 to a temperature greater than the inlet feed temperature to the first reactor 30, generating the heated feedstream 22. The heated feedstream 22 is split, as above, into two portions with the second portion 22b passed to a downstream interheater. The first portion 22a is combined with the second portion 16 of the preheated feedstream to reduce the temperature of the second portion 22a before passing the reactor feed to the first reactor 30.

The feed to the first reactor 30 comprises a combination of the first portion 22a of the heated feedstream and a second portion 16 of the preheated feedstream. This allows for heating the first portion 14 of the preheated feedstream to a temperature greater than the first reactor inlet temperature. The charge heater 20 can add additional heat to the first portion 14 wherein the added heat will be transferred to downstream reactors. A temperature indicator controller 26 will control the amount of the second portion 16 of the preheated feedstream to be mixed with the first portion 22a of the heated feedstream to being the temperature to the desired first reactor inlet temperature. This provides an advantage for utilizing excess capacity in the charge heater 20 to supplement heat to downstream reactors, without having to add additional heaters. Temperature indicator controllers can be utilized with downstream reactors for mixing a portion of effluent streams from upstream reactors with a portion of streams heated by interheaters.

The present invention is operated such that the first reactor is operated at a first inlet temperature and subsequent reactors are operated at a second inlet temperature greater than the first reactor inlet temperature. When referring to temperatures, for the reforming process, the controls refer to the inlet temperatures, as the temperature in the reactor declines as the reaction proceeds. The first inlet temperature is less than 540° C., with a preferred inlet temperature between 400° C. and 500° C., and with a more preferred temperature between 400° C. and 550° C. The second inlet temperature is greater than 500° C., with a preferred inlet temperature between 510° C. and 600° C., and with a more preferred temperature between 520° C. and 560° C.

In one aspect of the invention the inlet temperatures of the reactors are operated at successively increasing temperatures, with the inlet temperature of the first reactor between 450° C. and 520° C., and the temperature of the subsequent reactors between 500° C. and 600° C.

Figure 2:
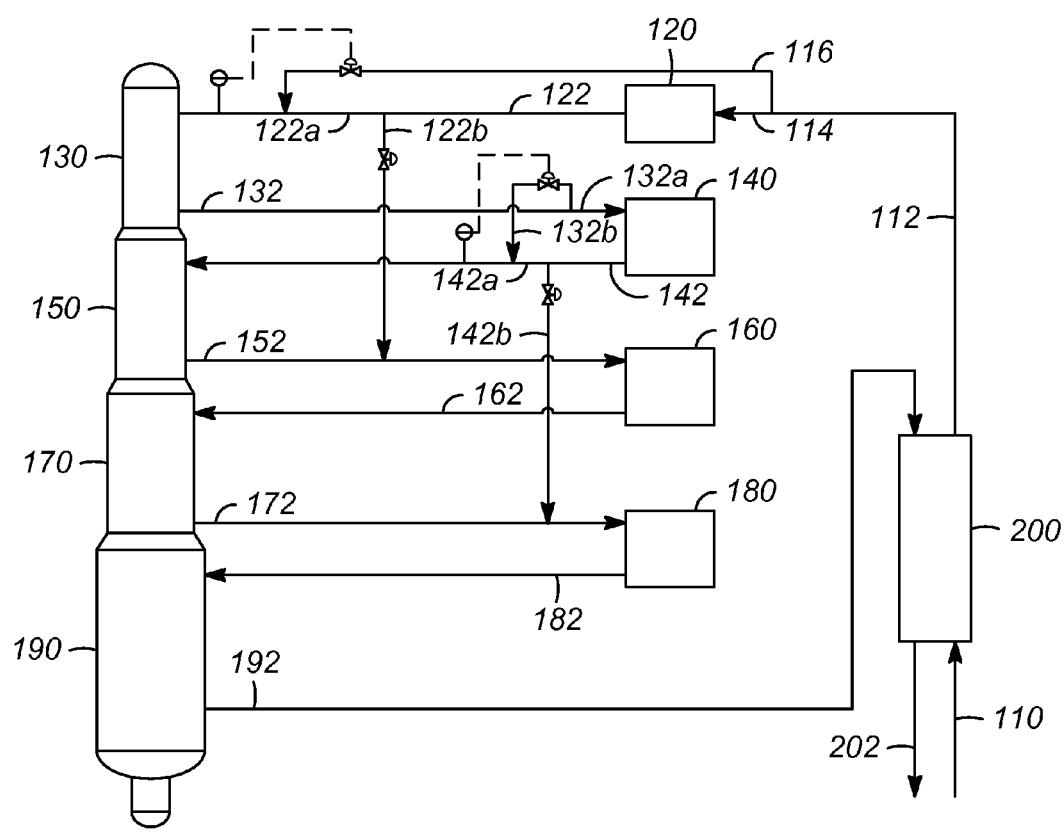
FIG. 2 is a diagram of a second embodiment of the invention for utilizing upstream reactors to heat feeds for downstream processing.

A second embodiment can be seen with FIG. 2. A hydrocarbon feedstream 110 is split into a first portion 114 and a second portion 116. The first portion 114 is passed through a charge heater 120 to generate a first heated feedstream 122. The first heated feedstream 122 is split into a first portion 122a and a second portion 122b. The first portion 122a of the heated feedstream is combined with the second portion 116 of the hydrocarbon feedstream, and the combined stream is passed to a first reactor 130 to generate a first reactor effluent stream 132. The first reactor effluent stream 132 is split into a first portion 132a and a second portion 132b. The first portion 132a is passed through a first reactor interheater 140 to generate a first heated effluent stream 142. The first heated effluent stream 142 is split into a first portion 142a and a second portion 142b. The first portion 142a and the second portion 132b are combined to form a second reactor 150 feedstream, and the second reactor 150 generates a second reactor effluent stream 152. The second reactor effluent stream 152 is combined with the second portion 122b of the first heated feedstream 122 and passed through a second reactor interheater 160 to generate a second heated effluent stream 162. The second heated effluent stream 162 is passed to a third reactor 170 to generate a third effluent stream 172. The third reactor effluent stream 172 is combined with the second portion 142b of the first heated effluent stream 142 and the combined stream is passed to a third reactor interheater 180 to generate a third heated effluent stream 182. The third heated effluent stream 182 is passed to a fourth reactor 190 to generate an effluent product stream 192.

The process can be further expanded to cover additional reactors and additional interheaters within a reforming reactor system.

The product stream 192 can further be passed to a combined feed heat exchanger 200 to generate a cooled product stream 202. The hydrocarbon feedstream 110 can be passed through the heat exchanger 200 to generate a preheated feedstream 112.

The process is designed to upgrade existing systems, by allowing the excess heat capacity to be passed downstream, and by operating the first reactor at a temperature below the temperatures of the subsequent reactors. In an alternate operation, each subsequent inlet reactor temperature is greater than the inlet reactor temperature of the preceeding reactor.

The temperature of operation is the inlet temperature of the first reactor feed, which is a combined feed of 122a and 166, and is typically a temperature between 450° C. and 540° C. The space velocity can be increased over normal commercial operating conditions. The reaction conditions include a liquid hour space velocity (LHSV) of the present invention in the range from 0.6 $hr^{-1}$ to 10 $hr^{-1}$. Preferably, the LHSV is between 0.6 $hr^{-1}$ and 5 $hr^{-1}$, with a more preferred value between 1 $hr^{-1}$ and 5 $hr^{-1}$. The catalyst also has a residence time in the reformer between 0.5 hours and 36 hours.

The present invention lowers the first inlet temperature to the first reactor to a temperature less than 540° C., with subsequent reactors having inlet temperatures greater than 540° C. The first reactor inlet temperature is preferred to be between 400° C. and 500° C., with a more preferred inlet temperature between 400° C. and 450° C. The inlet temperature to the subsequent reactors, or second and greater reactors in the series should be greater than 500° C., with a preferred inlet temperature between 510° C. and 600° C., and a more preferred inlet temperature between 520° C. and 560° C.

Due to the elevated temperature, the problems of potential increased thermal cracking can be addressed by having a shorter residence time of the hydrocarbon process stream in the equipment at the elevated temperature, or by moving higher temperatures to downstream reactors. The increased temperature can also increase coking on metallic surfaces of the transfer equipment and the reactor internals.

The process can also include adding compounds to change the ability to reduce the amount of coking. One example is the injection of a sulfur compound, such as HOS, into the feedstream. The presence of a small amount of sulfur reduces the coking in the high temperature reforming.

The reforming process is a common process in the refining of petroleum, and is usually used for increasing the amount of gasoline. The reforming process comprises mixing a stream of hydrogen and a hydrocarbon mixture and contacting the resulting stream with a reforming catalyst. The usual feedstock is a naphtha feedstock and generally has an initial boiling point of about 80° C. and an end boiling point of about 205° C. The reforming reaction converts paraffins and naphthenes through dehydrogenation and cyclization to aromatics. The dehydrogenation of paraffins can yield olefins, and the dehydrocyclization of paraffins and olefins can yield aromatics.

The reforming process is an endothermic process, and to maintain the reaction, the reformer is a catalytic reactor that can comprise a plurality of reactor beds with interbed heaters. The reactor beds are sized with the interbed heaters to maintain the temperature of the reaction in the reactors. A relatively large reactor bed will experience a significant temperature drop, and can have adverse consequences on the reactions. The interbed heaters reheat the process stream as the process stream flows from one reactor bed to a sequential reactor bed within the reformer reactor system. The most common type of interbed heater is a fired heater that heats the fluid and catalyst flowing in tubes. Other heat exchangers can be used.

Reforming catalysts generally comprise a metal on a support. The support can include a porous material, such as an inorganic oxide or a molecular sieve, and a binder with a weight ratio from 1:99 to 99:1. The weight ratio is preferably from about 1:9 to about 9:1. Inorganic oxides used for support include, but are not limited to, alumina, magnesia, titania, zirconia, chromia, zinc oxide, thoria, boria, ceramic, porcelain, bauxite, silica, silica-alumina, silicon carbide, clays, crystalline zeolitic aluminasilicates, and mixtures thereof. Porous materials and binders are known in the art and are not presented in detail here. The metals preferably are one or more Group VIII noble metals, and include platinum, iridium, rhodium, and palladium. Typically, the catalyst contains an amount of the metal from about 0.01% to about 2% by weight, based on the total weight of the catalyst. The catalyst can also include a promoter element from Group IIIA or Group IVA. These metals include gallium, germanium, indium, tin, thallium and lead.

While the invention has been described with what are presently considered the preferred embodiments, it is to be understood that the invention is not limited to the disclosed embodi-

The invention claimed is:

1. A process for increasing the aromatic content in a naphtha feedstream in reforming reactors in a series, comprising:

passing the naphtha feedstream through a series of reforming reactors and reactor feed heaters, wherein the reactors feed heaters generate a heated stream and at least one of the heated streams is split into a first portion and a second portion, with the first portion passed to a reforming reactor to generate a reforming reactor effluent stream; and wherein the second portion of the heated stream is combined with a downstream reforming reactor effluent stream and the combined stream is passed to a downstream reactor feed heater, to generate a reactor product stream by converting paraffins and naphthenes in the naphtha feedstream through dehydrogenation and cyclization in the presence of added hydrogen, added sulfur compounds and a reforming catalyst in reforming reactors to aromatics with increased aromatic content;

wherein the first reforming reactor is operated at a temperature between 400° C. and 500° C., and the following reactors are operated at a second reaction temperature between 500° C. and 600° C., wherein the following reaction temperatures is greater than the first reaction temperature, and wherein the reforming reactors are operated as successively greater temperatures.

2. The process of claim 1 further comprising:

splitting at least one reactor effluent stream into a first portion and a second portion;

passing the first portion of the effluent stream with the second portion of the heated stream to a reactor interheater; and combining the second portion of the effluent stream with a downstream heated feedstream to a downstream reactor.

3. The process of claim 2 wherein the downstream reactor is the next reactor in the series of reactors.

4. The process of claim 2 wherein the downstream reactor is the reactor after the next reactor in the series of reactors.

5. The process of claim 1 wherein the second reaction temperature is between 520° C. and 560° C.

* * * * *